US006291387B1

(12) United States Patent
Sen et al.

(10) Patent No.: US 6,291,387 B1
(45) Date of Patent: Sep. 18, 2001

(54) TRANSITION METAL-FREE OLEFIN POLYMERIZATION CATALYST

(75) Inventors: Ayusman Sen; Louis M. Wojcinski, II; Shengsheng Liu, all of State College, PA (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 09/273,128

(22) Filed: Mar. 19, 1999

Related U.S. Application Data

(60) Provisional application No. 60/078,695, filed on Mar. 20, 1998.

(51) Int. Cl.$^7$ .................................................. B01J 31/00
(52) U.S. Cl. ........................ 502/152; 502/155; 502/156; 502/164; 502/171
(58) Field of Search .................................... 502/156, 152, 502/155, 164, 171

(56) References Cited

U.S. PATENT DOCUMENTS

| | | | | |
|---|---|---|---|---|
| 2,744,074 | * | 5/1956 | Theobald | 260/2 |
| 2,825,721 | * | 3/1958 | Hogan et al. | 260/88.1 |
| 3,135,706 | * | 6/1964 | Vandenberg | 502/156 |
| 5,340,892 | * | 8/1994 | Kuramoto | 526/160 |
| 5,391,793 | * | 2/1995 | Marks et al. | 556/179 |
| 5,777,120 | * | 7/1998 | Jordan et al. | 502/152 |
| 5,939,346 | * | 8/1999 | Marks et al. | 502/125 |
| 5,962,362 | * | 10/1999 | Wasserman et al. | 502/155 |

FOREIGN PATENT DOCUMENTS

| | | | |
|---|---|---|---|
| 52-35192 | * | 3/1977 | (JP) ..................................... 502/156 |
| WO 94/10180 | * | 5/1994 | (WO) . |
| WO 96/23010 | | 8/1996 | (WO) . |
| WO 98/40421 | | 9/1998 | (WO) . |

OTHER PUBLICATIONS

Coles, et al, *Organometallics*, vol. 17, pp. 4042–4048 (1998).
Ihara, et al, *J. Am. Chem. Soc.*, vol. 120, pp. 8277–8278 (1998).
Bruce, et al, *J. Chem. Commun.*, p. 2523 (1998).
Small, et al, *J. Am. Chem. Soc.*, vol. 120, pp. 4049–4050 (1998).
Martin, et al, *Makromol. Chem.*, vol. 193, pp. 1283–1288 (1992).
Coles, et al, *J. Am. chem. Soc.*, vol. 119, pp. 8125–8126 (1997).
Johnson, et al, *J. Am. chem. Soc.*, vol. 117, pp. 6414–6415 (1995).
Coles, et al, *Organometallics*, vol. 16, pp. 5183–5194 (1997).
Aeilts, et al, *Organometallics*, vol. 17, pp. 3265–3270 (1998).
D.G. Hendershot et al., Organometallics, vol. 10, No. 6, pp. 1917–1922, 1991.*
Karol, et al, *J. Polym. Sci.*: Part A–1, vol. 10, pp. 2621–2637 (1972).
49 *Chem. Abs.* 3576e (Karl Ziegler, Polymerization of ethylene).
Doi, et al, *Makromol. Chem.*, vol. 180, pp. 1359–1361 (1979).
Sinn, et al, *Advances in Organometallic Chem.*, vol. 18, pp. 99–149 (1980).

* cited by examiner

*Primary Examiner*—Mark L. Bell
*Assistant Examiner*—J. Pasterczyk
(74) *Attorney, Agent, or Firm*—Anthony J. DeLaurentis

(57) ABSTRACT

Ethylene and/or propylene are polymerized to form high molecular weight, linear polymers by contacting ethylene and/or propylene monomer, in the presence of an inert reaction medium, with a catalyst system which consists essentially of (1) an aluminum alkyl component, such as trimethylaluminum, triethylaluminum, triisobutylaluminum, tri-n-octylaluminum and diethylaluminum hydride and (2) a Lewis acid or Lewis acid derivative component, such as B$(C_6F_5)_3$, $[(CH_3)_2N\,(H)\,(C_6H_5)]^+[B\,(C_6F_5)4]^-$, $[(C_2H_5)_3NH]^+[B\,C_6F_5)_4]^-$, $[C(C_6F_5)_3]^+[B(C_6F_5)_4]^-$, $(C_2H_5)_2Al(OCH_3)$, $(C_2H_5)_2Al(2,6$-di-t-butyl-4-methylphenoxide), $(C_2H_5)_2Al(2,6$ -di-t-butylphenoxide)$_2$, $(C_2H_5)_2Al(2,6$-di-t-butylphonoxide) , 2,6 -di-t-butylphenol·methylaluminoxane or an alkylaluminoxane, and which may be completely free any transition metal component(s).

4 Claims, No Drawings

TRANSITION METAL-FREE OLEFIN POLYMERIZATION CATALYST

RELATED APPLICATIONS

This application is based on Provisional Application No.60/078695, filed Mar. 20, 1998, the disclosure of which is incorporated herein by reference.

This application was funded under Department of Energy Contract No. DE-FG02-84ER1 3295.

BACKGROUND OF THE INVENTION

This invention relates to high molecular weight, highly linear polymers of ethylene and α-olefins, e.g., propylene, which are prepared in the presence of an aluminum-based catalyst system. More specifically, the invention relates to the synthesis of ethylene and α-olefin homopolymers and copolymers in an inert reaction medium in the presence of a catalyst system consisting essentially of an aluminum alkyl compound and an organo-Lewis acid. An advantage of the present invention is that it enables the synthesis of high molecular weight ethylene and α-olefin polymers without the need for transition metal catalysts, thereby avoiding disposal problems associated with the use of such catalysts.

It is known that the "aufbau" reaction, in which ethylene is reacted at high temperatures and high pressures to form higher olefins, occurs in two steps. In the first step, ethylene is exposed to a trialkyl aluminum compound at temperatures on the order of 90–120° C. and pressures of about 100 psi to form higher aluminum alkyls. In the second step, the temperature is raised to 150° C. to displace the higher alkyl groups and to form an α-olefin. While studying this reaction in the early 1950's, it was discovered that the addition to the reaction mass of earlier transition metal compounds, specifically titanium halides, resulted in the formation of high molecular polymers. Since that discovery, a variety of catalyst systems have been reported, using a variety of transition metals, including chromium (IV) oxides (Hogan, J. P., et al, U.S. Pat. No. 2,825,721), chromocenes (Karol, F. J., et al, *J. Polym. Sci., Part A*, 1972, 2621), and acetylacetonate complexes of vanadium (Doi, Y., et al, *Makromol. Chem.*, 1979, 180, 1359). Beginning in about 1980, a great deal of study was conducted in connection with highly active metallocene/methylaluminoxane (MAO) olefin polymerization catalyst systems, and more recently olefin polymerization catalysts based on diimine complexes of nickel and palladium have been reported. See, e.g., Sinn, H. and Kaminski, W., *Adv. Organomet. Chem.*, 1980, 18, 99; Johnson, L. K., et al, *J. Am. Chem. Soc.*, 1995, 117, 6414; Johnson, L. K., et al, Int. Pat. Appl. WO96/23010 (1996); and Small, B. L., et al, *J. Am. Chem. Soc.*, 1998, 120,4049.

For each of the known transition metal-based catalyst systems, it was believed that the transition metal played a vital role in the formation of high molecular weight polymers; and that in the absence of any transition metal, only oligomers would be produced, as in the aufbau reaction. To date, there have been few reports detailing the preparation of high molecular polymers of ethylene via transition metal-free catalyst systems. In 1992, Heinz Martin (a former student of Karl Ziegler) reported the sysnthesis of high molecular weight polyethylene by exposing ethylene to an aluminum alkyl catalyst over a period of several days (Martin, H., *Makromol. Chem.*, 1992, 193, 1283). More recently, the synthesis of cationic aluminum complexes bearing bulky imine type ligands, as well as their potential utility as ethylene polymerization catalysts, has been investigated. See, e.g., Coles, M. P., et al, *J. Am. Chem. Soc.*, 1997, 119, 8125; Coles, M. P., et al, Int. Pat. Appl. WO98/40421; Coles, M. P., et al, *Organometallics*, 1997, 16, 5183; Aielts, S. L., et al, *Organometallics*, 1998, 17, 3265; Coles, M. P., et al, *Organometallics*, 1998, 17, 4042; Ihara, E., et al, *J. Am. Chem. Soc.*, 1998, 120, 8277; Bruce, M., et al, *J. Chem. Commun.*, 1998, 2523; and U.S. Pat. No. 5,777,120.

While great strides have been made in the search for new and improved ethylene and α-olefin polymerization catalysts, there remains a need for catalyst systems that are free from transition metals, that comprise only commercially available components, that require no ligand substitution, and that, nonetheless, are capable of efficiently converting monomer to high molecular weight polymer under otherwise conventional polymerization reaction conditions.

SUMMARY OF THE INVENTION

In accordance with the present invention, the need for transition metal-free olefin polymerization catalysts has been met by providing a catalyst system that comprises two essential components, namely: (1) an aluminum alkyl component, and (2) a Lewis acid or Lewis acid derivative component that is capable of activating the aluminum alkyl component.

The aluminum alkyl component may be illustrated by the formula $AlR_xH_{3-x}$, where R is an alkyl group, and $0 < x \leq 3$. Aluminum alkyl compounds that are suitable for use in this invention include, for example, trimethylaluminum, triethylaluminum, triisobutylaluminum, tri-n-octylaluminum and diethylaluminum hydride.

The Lewis acid or Lewis acid derivative component, hereinafter sometimes referred to as the "Lewis acid component", contemplated for use in the present invention includes, for example, Tris-(pentafluorophenyl) boron (designated herein as "FAB" and having the formula $B(C_6F_5)_3$), tri(phenyl)methyl tetra(pentafluorophenyl)borate (designated herein as "Trityl FAB" and having the formula $[(C_6F_5)_3C]^+[B[(C_6F_5)_4]^{31}$ ), N,N-dimethylanilinium tetra (pentafluorophenyl)borate (designated herein as "Anilinium FAB" and having the formula $[(CH_3)_2N(H)(C_6H_5)]^+$-$[B[(C_6F_5)_4]^-$) or a conventional alkylaluminoxane, such as methylaluminoxane (designated herein as "MAO" and having the formula $—(Al(CH_3)O)_n)—$.

MAO, which is the product of the hydrolysis of trimethylaluminum, contains as much as 30% unreacted aluminum trialkyl. Accordingly, it is within the scope of this invention to use MAO as both the aluminum alkyl component and as the Lewis acid component of the catalyst system. However, in such case, it is preferable to add an aluminum alkyl component and/or a Lewis acid component in addition to the MAO. Similarly, it is also within the scope of this invention to use an alkylaluminoxane in conjunction with an alcohol or phenol adduct of an alkylaluminoxane. For example, a suitable catalyst system in accordance with this invention would comprise MAO in combination with 2,6-di-t-butylphenol·MAO.

The catalyst system of this invention is indeed capable of polymerizing ethylene and α-olefins, particularly propylene, under conventional reaction conditions, and results in the formation of high molecular weight, highly linear polymers having narrow polydispersities, indicative of a "single site" catalyst.

The polymerization typically is carried out by contacting the selected monomer (e.g., ethylene and/or propylene) in an inert polar solvent (e.g., chlorobenzene) or hydrocarbon solvent (e.g., toluene) at a temperature of about 20 to 150° C., typically from about 50 to about 120° C., e.g. 50° C., and a pressure of from about 50 to about 1,500 psi, typically from about 400 to about 800 psi, e.g., 800 psi. The polymerization reaction typically would be allowed to proceed for a period of from about 1 hour to about 24 hours, after which the polymerization reaction would be terminated by conventional means, e.g., by adding methanol or another conventional polymerization stopper to the reaction mass.

DESCRIPTION OF PREFERRED EMBODIMENTS

The preparation of high molecular weight, essentially linear polymers (as determined by $^1$H and $^{13}$C-NMR and by a melting point greater than 133° C.) of ethylene and α-olefins, e.g., propylene, is achieved in accordance with one preferred aspect of the invention by contacting ethylene and/or propylene, in the presence of an inert solvent, and under polymerization reaction conditions, with a catalyst which comprises (1) an alkylaluminum component and (2) a Lewis acid or Lewis acid derivative component as the only essential components.

The monomers that may be polymerized in accordance with this invention include ethylene and propylene, as well as other α-olefins, such as hexene.

The monomers may be polymerized singly to form homopolymers, such as polyethylene or polypropylene. In the alternative, two or more monomers may be mixed and polymerized simultaneously to form copolymers, such as ethylene-propylene copolymers. Typically, the present invention would be used to prepare polyethylene and polypropylene products having a number average molecular weight ($M_n$), determined relative to polystyrene standards, on the order of from about 5,000 to about 500,000, preferably from about 20,000 to about 200,000. The resulting polymer products would be highly linear and would be characterized by a narrow polydispersity ($M_w/M_n$), typically on the order of from about 1.5 to about 2.5, indicative of a single site catalyst.

The polymerization preferably is carried out in the presence of an inert solvent, with polar solvents, such as chlorobenzene, being preferred over hydrocarbon solvents, such as toluene, inasmuch as the use of polar solvents has been found to result in a higher yield of polymer product. Polar solvents which may be used in lieu of chlorobenzene, or in addition to chlorobenzene include, for example, dichlorobenzene, trichlorobenzene and tetrachloroethane.

Hydrocarbon solvents which may be used in lieu of toluene, or in addition totoluene include, for example, benzene, xylene and hexane.

The polymerization typically is carried out by contacting the selected monomer and the catalyst system at a temperature of about 20 to 150° C., typically from about 50 to about 120° C., e.g. 50° C., and a pressure of from about 50 to about 1,500 psi, typically from about 400 to about 800 psi, e.g., 800 psi. The polymerization may be performed in conventional apparatus and in a conventional manner, except that the present catalyst system would be used in place of the currently employed transition metal-based catalyst systems. The polymerization may be performed in a continuous process, a semi-continuous process, or a batch process, as desired, Typically, the polymerization would be allowed to proceed for a period of from about 1 hour to about 24 hours, after which the polymerization reaction would be terminated by conventional means, e.g., by adding methanol or another conventional polymerization stopper to the reaction mass.

The catalyst system of this invention does not require the presence of a transition metal component. The only essential components of the catalyst system are (1) an aluminum alkyl component and (2) a Lewis acid or Lewis acid derivative component that is capable of activating the aluminum alkyl component.

The aluminum alkyl component may be any conventional aluminum alkyl and may be illustrated by the formula $AlR_xH_{3-x}$ where R is an alkyl group, typically a $C_1$–$C_{10}$ alkyl group, and $0<x\leq3$. Aluminum alkyl compounds that are suitable for use in this invention include, for example, trimethylaluminum, triethylaluminum, triisobutylaluminum, and tri-n-octylaluminum and diethylaluminum hydride.

As used in this specification and claims, the term "Lewis acid or Lewis acid derivative" is meant to describe any relative strong Lewis acid or Lewis acid derivative that is capable of activating the aluminum alkyl component to the extent that the desired polymerization will occur with reasonable efficiency. Typically, the Lewis acid or Lewis acid derivative will be selected such that the polymerization activity of the resulting catalyst system is on the order of from about 0.01 to about 100 kg/mol catalyst·hr.

In keeping with this requirement, Lewis acids and Lewis acid derivatives which have been found to be particularly suitable for use in this invention include, for example, Tris-(pentafluorophenyl) boron (designated herein as "FAB" and having the formula $B(C_6F_5)_3$)), tri(phenyl)methyl tetra (pentafluorophenyl)borate (designated herein as "Trityl FAB" and having the formula $[(C_6F_5)_3C]^+[B[(C_6F_5)_4]^{31}$ ), and N,N-dimethylanilinium tetra(pentafluorophenyl)borate (designated herein as "Anilinium FAB" and having the formula $[(CH_3)_2N(H)(C_6H_5)]^+[B[(C_6F_5)_4]^-)$. Additional, non-limiting examples of Lewis acids or Lewis acid derivatives that may be used as part of the present catalyst system include, for example, diethylaluminum methoxide $(C_2H_5)_2$ Al(OCH$_3$), diethylaluminum-2,6-di-t-butyl-4-methylphenoxide $(C_2H_5)_2$Al(2,6-di-t-butyl-4-methylphenoxide), ethylaluminum-di-(2,6-di-t-butyl-4-methylphenoxide) $(C_2H5)Al(2,6$-di-t-butylphenoxide)$_2$, diethylaluminum-(2,6-di-t-butylphenoxide) $(C_2H_5)_2Al(2,6$-di-t-butylphenoxide, as well as conventional alkylaluminoxanes, such as methylaluminoxane (designated herein as "MAO" and having the formula —(Al(CH$_3$)O)$_n$)—).

It should be noted that the alkylaluminoxanes, which are the product of the hydrolysis of a trialkylaluminum, e.g., trimethylaluminum in the case of MAO, and which contain as much as 30% unreacted trialkylaluminum, function both as the aluminum alkyl component and as the organo-Lewis acid component of the catalyst system. Accordingly, it is within the scope of this invention to use an alkylaluminoxane as the sole catalyst component. However, when use is made of an alkylaluminoxane as a catalyst component of this invention, it is preferable to add an aluminum alkyl component in addition to the alkylaluminoxane. Similarly, it is also within the scope of this invention to use an alkylaluminoxane component in conjunction with an alcohol or phenol adduct of an alkylaluminoxane. For example, a suitable catalyst system in accordance with this latter aspect of the invention would comprise MAO in combination with the 2,6-di-t-butylphenol·MAO adduct.

The invention will be appreciated more fully in light of the following examples, which are intended merely to illustrate the invention, and not to limit the scope thereof.

Example 1

Ethylene polymerization via transition metal-free catalyst.

In a series of polymerization runs, ethylene was polymerized at 50° C. in the presence of the catalyst system and reaction solvent indicated in Table 1. Each polymerization run was carried out in a stainless steel 125 ml pressure vessel equipped with a glass liner. For most runs, the catalyst system, mixed in 10 ml of solvent, was introduced into the pressure vessel in a nitrogen-filled glove box. Then, after removing the assembled pressure vessel from the glove box, the vessel was charged with 800 psi ethylene (single charge), and the reaction was allowed to continue for the indicated time. The reaction vessel was then vented, and the reaction mixture was poured, with stirring, into acidic methanol to kill the polymerization. The polymer was stirred overnight, filtered, and vacuum dried overnight. For each run, the resulting polymer was analyzed for yield, activity, number average molecular weight ($M_n$) and weight average molecular weight ($M_w$). The data observed for each run is set forth in Table 1.

carried in a stainless steel 125 ml pressure vessel equipped with a glass liner. For each run, the catalyst system, mixed in 10 ml of solvent, was introduced into the pressure vessel in a nitrogen-filled glove box. Then, after removing the assembled pressure vessel from the glove box, the vessel was charged with 5 grams of propylene (single charge), and the reaction was allowed to continue at 50° C. for 20 hours

TABLE 1

Ethylene polymerization via transition metal-free catalysis

| Run No. | Catalyst | Components | Solvent | Yield (g) | Activity (kg/mol catalyst · hr) | $M_n$ ($\times 10^{-3}$)[o] | $M_w$ ($\times 10^3$) |
|---|---|---|---|---|---|---|---|
| 1 | Al(C$_2$H$_5$)$_3$[a] | MAO[h] | C$_6$H$_5$Cl | 3.9 | 3.25 | 40 | 98 |
|   |   |   |   |   |   | 111[b] | 263 |
| 2 | Al(C$_2$H$_5$)$_3$[a] | MAO[h] | Toluene | 0.6 | 0.50 |   |   |
| 3 | MAO[a,h] | FAB[i] | C$_6$H$_5$Cl | 0.4 | 0.35 | 282 | 486 |
| 4 | Al(C$_2$H$_5$)$_3$[a] | FAB[i] | C$_6$H$_5$Cl | 1.0 | 0.85 |   |   |
| 5 | Al(C$_2$H$_5$)$_3$[a] | Trityl FAB[j] | C$_6$H$_5$Cl | 2.8 | 2.46 |   |   |
| 6 | Al(C$_2$H$_5$)$_3$[a] | an. FAB[k] | C$_6$H$_5$Cl | 1.1 | 1.03 |   |   |
| 7 | Al(CH$_3$)$_3$[a] | MAO[h] | C$_6$H$_5$Cl | 1.5 | 1.25 |   |   |
| 8 | (i-C$_4$H$_9$)$_2$AlH[a] | FAB[i] | C$_6$H$_5$Cl | 0.6 | 0.50 |   |   |
| 9 | MAO[c,h] | FAB[i] | Toluene | 1.2 | 1.00 |   |   |
| 10 | MAO[c,h] | an. FAB[k] | C$_6$H$_5$Cl | 0.9 | 0.75 |   |   |
| 11 | MAO[d,h] | (C$_2$H$_5$)$_2$Al(OC$_2$H$_5$) | C$_6$H$_5$Cl | 0.3 | 0.01 |   |   |
| 12 | MAO[e,h] | (C$_2$H$_5$)Al(dtbmp)[l] | C$_6$H$_5$Cl | 0.2 | 0.02 |   |   |
| 13 | MAO[f,h] | (C$_2$H$_5$)Al(dtbp)[m] | C$_6$H$_5$Cl | 2.4 | 0.13 |   |   |
| 14 | MAO[g,h] | (C$_2$H$_5$)Al(dtbp)[m] | C$_6$H$_5$Cl | 4.7 | 1.04 |   |   |
| 15 | MAO[f,h] | dtbp · MAO[n] | C$_6$H$_5$Cl | 2.5 | 0.14 |   |   |

Reaction conditions run with 800 psi ethylene (single charge).
[a]= 0.3 mmol each catalyst component, 50° C., 4 hrs., 10 ml solvent.
[b]= Run for 20 hrs. Reaction run for 20 hrs.
[c]= 0.4 mmol each catalyst component, 50° C., 4 hrs., 20 ml solvent.
[d]= 3 mmols each catalyst component, 60° C., 10 hrs., 10 ml solvent.
[e]= 2 mmol each catalyst component, 5 hrs.
[f]= 2 mmol each catalyst component, 9 hrs.
[g]= 0.5 mmol each catalyst component, 9 hrs.
[h]= MAO = methylaluminoxane.
[i]= FAB = B(C$_6$F$_5$)$_3$ = Tris(pentafluorophenyl)boron.
[j]= Trityl FAB = [(C$_6$F$_5$)$_3$C]$^+$[B[(C$_6$F$_5$)$_4$]$^-$ = Tri(phenyl)methyltetra(pentafluorophenyl)borate.
[k]= an. FAB = Anilinium FAB = [(CH$_3$)$_2$N(H)(C$_6$H$_5$)]$^+$[B[(C$_6$F$_5$)$_4$]$^-$ = N,N-dimethylanilinium tetra (pentafluorophenyl)borate.
[l]= dtbmp = 2,6-di-t-butyl-4-methylphenoxide.
[m]= dtbp = 2,6-di-t-butylphenoxide.
[n]= adduct of MAO with 1 eq. 2,6-di-t-butylphenol.
[o]= Determined relative to polystyrene standards.

Example 2

Propylene polymerization

In a series of polymerization runs, propylene was polymerized in the presence of the catalyst system and reaction solvent indicated in Table 2. Each polymerization run was carried in the presence of 0.3 mmol of each catalyst component indicated in Table 2. The reaction vessel was then vented, and the reaction mixture was poured, with stirring, into acidic methanol to kill the polymerization. The polymer was stirred overnight, filtered, and vacuum dried overnight. For each run, the resulting polymer was analyzed for yield, activity, number average molecular weight ($M_n$) and weight average molecular weight ($M_w$). The data observed for each run is set forth in Table 2.

TABLE 2

Propylene polymerization

| Run No. | Catalyst | Components | Solvent | Yield (g) | Activity (kg/mol catalyst · hr) | $M_n$[c] ($\times 10^{-3}$)[o] | $M_w$ ($\times 10^3$) |
|---|---|---|---|---|---|---|---|
| 1 | Al(C$_2$H$_5$)$_3$ | B(C$_6$F$_5$)$_3$ | C$_6$H$_5$Cl | 0.71 | 0.10 | 74 | 140 |
| 2 | MAO[a] | B(C$_6$F$_5$)$_3$ | Toluene | 0.95 | 0.13 | 112 | 229 |
| 3 | Al(CH$_3$)$_3$ | B(C$_6$F$_5$)$_3$ | C$_6$H$_5$Cl | 0.20 | 0.03 |   |   |
| 4 | (i-Butyl)$_2$AlH | an. FAB[b] | C$_6$H$_5$Cl | 0.07 | 0.01 |   |   |

Reactions were run with a single 5 gram charge of propylene.
[a]= MAO = methylaluminoxane.
[b]= an. FAB = Anilinium FAB = [(CH$_3$)$_2$N(H)(C$_6$H$_5$)]$^+$[B[(C$_6$F$_5$)$_4$]$^-$ = N,N-dimethylanilinium tetra (pentafluorophenyl)borate.
[c]= Determined relative to polystyrene standards.

Example 3

Ethylene/propylene copolymerization using an FAB/ Al(C$_2$H$_5$)$_3$

In a series of polymerization runs, ethylene and propylene was copolymerized at 60° C. in the presence of the catalyst system and reaction solvent indicated in Table 3. Each polymerization run was carried in a stainless steel 125 ml pressure vessel equipped with a glass liner. For each run, the catalyst system, mixed in 10 ml of solvent, was introduced into the pressure vessel in a nitrogen-filled glove box. Then, after removing the assembled pressure vessel from the glove box, the vessel was charged with the indicated pressures of ethylene and propylene (single charge for each), and the reaction was allowed to continue for the indicated time. The reaction vessel was then vented, and the reaction mixture was poured, with stirring, into acidic methanol to kill the polymerization. The polymer was stirred overnight, filtered, and vacuum dried overnight. For each run, the resulting polymer was analyzed for yield, activity, and melting point. The data observed for each run is set forth in Table 3.

TABLE 3

Ethylene/propylene copolymerization

| Run | Ethylene (psi) | Propylene (psi) | Time (hrs.) | Yield (g) | $T_m$ (melting point) (° C.) | Propylene (mol %) |
|---|---|---|---|---|---|---|
| 1 | 700 | 0 | 1.5 | 1.84 | 135.9 | 0 |
| 2 | 400 | 100 | 5 | 4.39 | 121.6 | 4.67 |
| 3 | 300 | 100 | 5 | 2.50 | 115.6 | 5.40 |
| 4 | 150 | 100 | 5 | 0.70 | 108.5 | 5.88 |
| 5 | 50 | 100 | 5 | 0.05 | 53.4 | 16.9 |

Conditions for each run: 10 ml chlorobenzene solvent; 0.1 mmol anililinium FAB=[(CH$_3$)$_2$N(H)(C$_6$H$_5$)]$^+$[B[(C$_6$F$_5$)$_4$]$^-$=N,N-dimethylanilinium tetra(pentafluorophenyl) borate, and 0.1 mmol Al(C$_2$H$_5$)$_3$; single charge ethylene/propylene.

What is claimed is:

1. A transition metal-free catalyst system for synthesizing high molecular weight, linear polymers of ethylene and α-olefins, consisting essentially of (1) an aluminum alkyl component represented by the formula AlR$_x$H$_{3-x}$, where R is an alkyl group and 0 is less than x and x is less than or equal to 3; and (2) a Lewis acid or Lewis acid derivative component capable of activating said aluminum alkyl component such that the polymerization activity of the resulting catalyst system is on the order of from about 0.01 to about 100 kg/mol catalyst·hr., said Lewis acid or Lewis acid derivative being selected from the group consisting of (a) B(C$_6$F$_5$)$_3$, (b) [(CH$_3$)$_2$N (H) (C$_6$H$_5$)]$^+$[B (C$_6$F$_5$)$_4$]$^-$, (C)[(C$_2$H$_5$)$_3$NH]$^+$[B (C$_6$F$_5$)$_4$]$^-$, (d) [C(C$_6$F$_5$)$_3$]$^+$[B(C$_6$F$_5$)$_4$]$^-$, (e) (C$_2$H$_5$)$_2$Al (OCH$_3$), (f) (C$_2$H$_5$)$_2$Al-(2,6-di-t-butyl-4-methylphenoxide), (g) (C$_2$H$_5$)Al(2,6-di-t-butylphenoxide)$_2$, (h) (C$_2$H$_5$)$_2$Al(2,6-di-t-butylphenoxide, (i) 2,6-di-t-butylphenol·methylaluminoxane, (j) an alkylaluminoxane, and mixtures thereof.

2. The transition metal-free catalyst system according to claim 1, wherein said Lewis acid or Lewis acid derivative component (2) is an alkylaluminoxane that contains unreacted aluminum trialkyl (1a), such that said alkylaluminoxane functions as both a portion of said aluminum alkyl component (1) and said Lewis acid or Lewis acid derivative component (2) of said catalyst system, and wherein additional aluminum alkyl component (1b) is present in said catalyst system such that the unreacted aluminum trialkyl (1a) and the additional aluminum alkyl component (1b), together, function as said aluminum alkyl component (1).

3. The transition metal-free catalyst system according to claim 1, wherein said alkylaluminoxane is selected from the group consisting of methylaluminoxane and an alcohol or phenol adduct of an alkylaluminoxane.

4. The transition metal-free catalyst system according to claim 3, wherein said alcohol or phenol adduct comprises 2,6-di-t-butylphenol·emethylaluminoxane.

* * * * *